United States Patent
Emura et al.

(10) Patent No.: US 7,799,783 B2
(45) Date of Patent: Sep. 21, 2010

(54) METHOD OF ADMINISTRATING AN ANTICANCER DRUG CONTAINING α, α, α-TRIFLUOROTHYMIDINE AND THYMIDINE PHOSPHORYLASE INHIBITOR

(75) Inventors: Tomohiro Emura, Hanno (JP); Akira Mita, Tokyo (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 688 days.

(21) Appl. No.: 11/042,059

(22) Filed: Jan. 26, 2005

(65) Prior Publication Data

US 2006/0167031 A1 Jul. 27, 2006

(51) Int. Cl.
*A61K 31/535* (2006.01)
(52) U.S. Cl. .................................. 514/235.8
(58) Field of Classification Search ............... 514/235.8
See application file for complete search history.

(56) References Cited

U.S. PATENT DOCUMENTS

| | | | |
|---|---|---|---|
| 5,744,475 A | 4/1998 | Yano et al. | |
| 6,159,969 A | 12/2000 | Yano et al. | |
| 6,294,535 B1 * | 9/2001 | Yano et al. | 514/235.8 |

FOREIGN PATENT DOCUMENTS

JP 3088757 7/2000

OTHER PUBLICATIONS

Fukushima et al. Structure and acitivty of specific inhibitors of thymidine phosphorylase to potentiate the function of antitumor 2'-deoxyribonucleosides. Biochemical Pharmacology, 2000, vol. 59, pp. 1227-1236.*
Freireich et al. Cancer Chemotherapy Reports, 1966, vol. 50, No. 4, pp. 219-244.*
Jerry A. Bell, et al., "Physical and Inorganic Chemistry", Journal of the American Chemical Society, vol. 84, No. 18, Sep. 28, 1962, pp. 3417, 3597-3598.
Charles Heidelberger, et al., "Syntheses of 5-Trifluoromethyluracil and 5-Trifluoromethyl-2'-deoxyuridine[1,2]", Journal of Medicinal Chemistry, vol. 7, No. 1, Jan. 8, 1964, pp. 1-5.
Jens W. Eckstein, et al., "Mechanism-Based Inhibition of Thymidylate Synthase by 5-(Trifluoromethyl)-2'-deoxyuridine 5'-Monophosphate", Biochemistry, vol. 33, No. 50, 1994, pp. 15086-15094.
Philip Reyes, et al., "Fluorinated Pyrimidines XXVI. Mammalian Thymidylate Synthetase: Its Mechanism of Action and Inhibition by Fluorinated Nucleotides", Mol. Pharmacol. vol. 1, 1965, pp. 14-31.
Patrick G. Johnston, et al., "The Role of Thymidylate Synthase Expression in Prognosis and Outcome of Adjuvant Chemotherapy in Patients With Rectal Cancer", Journal of Clinical Oncology, vol. 12, No. 12, Dec. 1994, pp. 2640-2647.
Heinz-Josef Lenz, et al., "Thymidylate Synthase mRNA Level in Adenocarcinoma of the Stomach: A Predictor for Primary Tumor Response and Overall Survival", Journal of Clinical Oncology, vol. 14, No. 1, Jan. 1995, pp. 176-182.
Patrick G. Johnston, et al., "Thymidylate Synthase protein Expression in Primary Colorectal Cancer: Lack of Correlation With Outcome and Response to Fluorouracil in Metastatic Disease Sites", Journal of Clinical Oncology, vol. 21, No. 5, Mar. 1, 2003, pp. 815-819.
Daniel L. Dexter, et al., "The clinical Pharmacology of 5-Trifluoromethyl-2'-deoxyuridine", Cancer Research, vol. 32, Feb. 1972, pp. 247-253.
Fred J. Ansfield, et al., "Phase I and II Studies of 2'-Deoxy-5(trifluoromethyl)-Uridine (NSC-75520)[1,2]", Cancer Chemotherapy Reports Part 1, vol. 55, No. 2, Apr. 1971, pp. 205-208.
Tomohiro Emura, et al., "A novel combination antimetabolite, TAS-102, exhibits antitumor activity in FU-resistant human cancer cells through a mechanism involving FTD incorporation in DNA", International Journal of Oncology, vol. 25, 2004, pp. 571-578.
Tomohiro Emura, et al., "An optimal dosing schedule for a novel combination antimetabolite, TAS-102, based on its intracellular metabolism and its incorporation into DNA", International Journal of Molecular Medicine, vol. 13, 2004, pp. 249-255.

* cited by examiner

*Primary Examiner*—James D Anderson
(74) *Attorney, Agent, or Firm*—Oblon, Spivak, McClelland, Maier & Neustadt, L.L.P.

(57) ABSTRACT

The present invention relates to a method for treating a cancer comprising orally administering a composition containing α,α,α-trifluorothymidine (FTD) and 5-chloro-6-(1-(2-iminopyrrolidinyl)methyl)uracil hydrochloride in a molar ratio of 1:0.5 at a dose of 20 to 80 mg/m²/day in terms of FTD in 2 to 4 divided portions per to patients in need of the treatment.

12 Claims, 3 Drawing Sheets

Trial 3

Trial 4

METHOD OF ADMINISTRATING AN ANTICANCER DRUG CONTAINING α, α, α-TRIFLUOROTHYMIDINE AND THYMIDINE PHOSPHORYLASE INHIBITOR

FIELD OF THE INVENTION

The present invention relates to a method for treating cancer, providing an increased therapeutic effect against cancer, which comprises administering an anticancer drug that uses α,α,α-trifluorothymidine (FTD) and a thymidine phosphorylase inhibitor (TPI) in combination.

BACKGROUND OF THE INVENTION

α,α,α-Trifluorothymidine (FTD, see the structural formula below) is a nucleoside analogue with substitution of a methyl group to trifluoromethyl group at the 5-position of thymidine, which was synthesized by Heidelberger et al. (J. Am. Chem. Soc., 84: 3597-3598, 1962; J. Med. Chem., 7: 1-5, 1964).

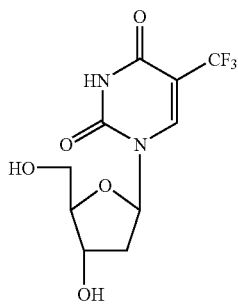

[Formula 1]

Unlike a fluorouracil (FU)-based antitumor drug that are widely used for cancer patients, FTD has no effect on RNA, and is phosphorylated by an intracellular thymidine kinase to form a monophosphorylated form, namely, trifluorothymidine monophosphate ($F_3TMP$). The $F_3TMP$ binds to a thymidylate synthase (TS) to exhibit a DNA synthesis-inhibiting effect (Biochemistry, 33: 15086-15094, 1994; Mol. Pharmacol., 1: 14-30, 1965). FU-based antitumor drug such as 5-FU that are clinically used as a representative antitumor drug have been reported to show a inhibition of TS activity as the main mechanism of action, while it has recently been reported that some patients are less sensitive to the FU-based antitumor agent (J. Clin. Oncol., 12: 2640-2647, 1994; Id. 14: 176-182, 1996; Id. 21: 815-819, 2003). The incorporation of FTD into DNA may represent an antitumor activity to FU less sensitive pacients by different mechanism of action from FU-based antitumor drug. Clinical trials of FTD were performed in 1970s, revealing the problem inherent in FTD that this drug is degraded by a thymidine phosphorylase (TP) in a human body after intravenous administration, resulting in the extremely shortened half-life thereof in the blood, i.e. approximately 12 minutes (Cancer Res., 32: 247-253, 1972). Further, although some tumor regressions were noted by divided doses every three hours, several problems have been also indicated that this means of administration lacks general usage, have showed adverse invent of the bone marrow supression and gastrointentinal toxicities, and have not necessarily been able to contribute to survival period even in some patients having tumor shrinkage (Cancer Chemother. Rep., 55: 205-208, 1971).

Under the circumstances, the applicant has discovered 5-chloro-6-(1-(2-iminopyrrolidinyl)methyl)uracil hydrochloride (see the structural formula below), a thymidine phosphorylase inhibitor (TPI) for preventing FTD degradation, which enables the blood concentration of FTD to be maintained and the drug to be administered orally for improving the general usage, and has developed a anticancer drug (TAS-102) containing FTD and TPI in a molar ratio of 1:0.5 (Japanese Patent No. 3,088,757; International Journal of Oncology 25: 571-578, 2004).

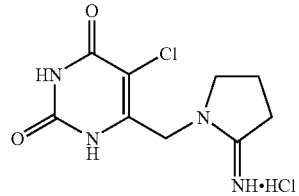

[Formula 2]

A phase I clinical trial of the combination drug was carried out in USA, starting by once-a-day oral dosing, to confirm that the blood FTD concentration was maintained and thus the combination drug is susceptible of oral administration. However, the resultant therapeutic effect of this combination drug against cancer was not satisfactory in the trial.

SUMMARY OF THE INVENTION

Accordingly, the present inventors modified the dosing schedule 2 to 3 times daily in tumor-bearing mice for the combination drug, resulting in a significantly increased antitumor activity compared to the once-a-day oral dosing there of despite the same total daily dosage used (International Journal of Molecular Medicine 13: 249-255, 2004). As a result of further administration at a daily oral dose in 2 to 4 divided portions to humans, the present invention was accomplished by the fact that, once-a-day administration was required dose of 100 mg/m$^2$/day (as a dose of FTD) for seeing the effect, in contrast, this divided dosing schedule showed higher effect at a dose as low as 20 to 80 mg/m$^2$/day.

In other words, the present invention provides a method for treating cancer, comprising administering to patients in need of cancer therapy a composition (hereinafter referred to as TAS-102) containing FTD and 5-chloro-6-(1-(2-iminopyrrolidinyl)methyl)uracil hydrochloride (hereinafter referred to as TPI-1) in a molar ratio of 1:0.5, at an oral dose of 20 to 80 mg/m$^2$/day in terms of FTD in 2 to 4 divided portions.

The present invention also provides a preparation for oral use containing α,α,α-trifluorothymidine and 5-chloro-6-(1-(2-iminopyrrolidinyl)methyl)uracil hydrochloride in a molar ratio of 1:0.5 wherein the preparation is packaged so that the dose of 20 to 80 mg/m$^2$/day may be administered in 2 to 4 divided portions to patients in need of cancer therapy.

According to the method of this invention, a more favorable therapeutic effect against cancer may be obtained despite the lower total daily dose compared to the once-a-day administration.

BRIEF DESCRIPTION OF THE DRAWINGS

FIG. 2 is a pair of diagrams showing a comparison of therapeutic effects on gastrointensinal cancer patients between thrice- and once-a-day oral administrations of a TAS-102 preparation containing FTD and TPI-1 (PD: progressive disease, SD: stable disease, MR: minor response, and PR: partial response). The ordinate axes represent individual patients and the horizontal axes represent the number of treatment courses. One treatment course consists of two cycles of daily dosing for 5 days followed by 2 days off treatment in the week, and subsequent 2 weeks off treatment, taking 4 weeks in total. However, the period of the off treatment may be prolonged stepwise if necessary, e.g. depending on the condition of a patient, the degree of side effect or the like.

DETAILED DESCRIPTION OF THE INVENTION

Figure 1:
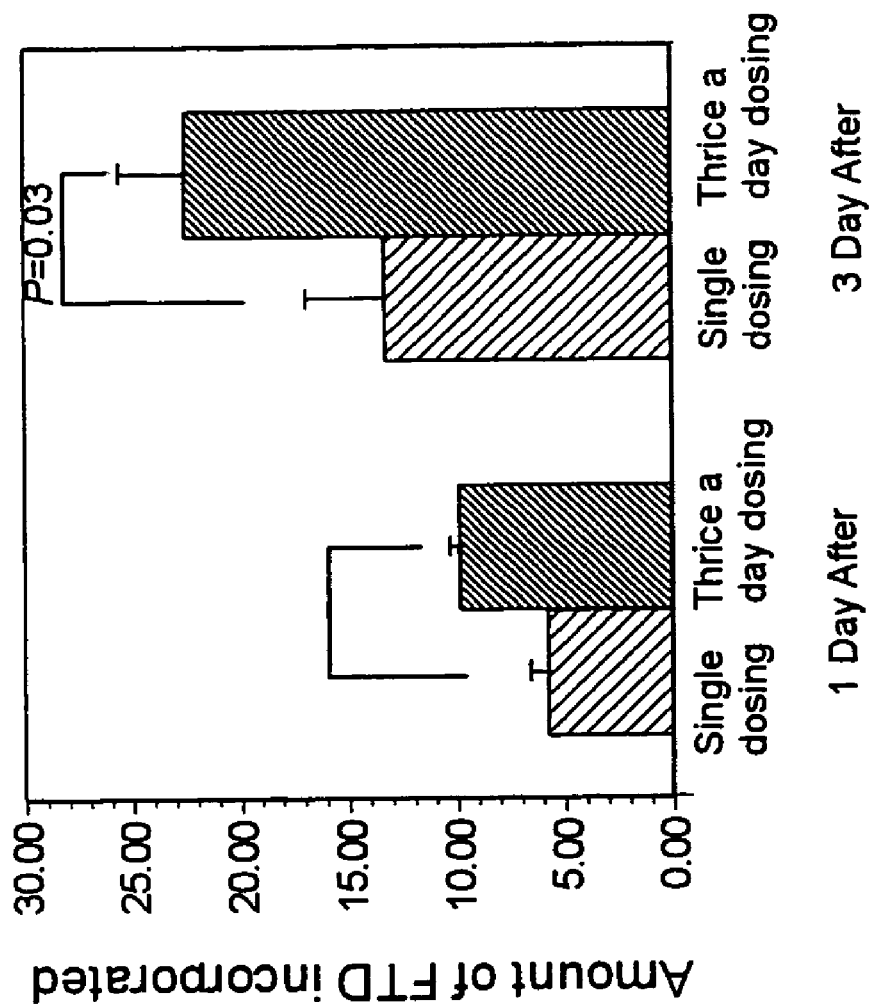
FIG. 1 is a bar graph showing the amount of FTD incorporated into DNA when a composition containing FTD and TPI-1 was orally administered once or thrice a day human gastric cancer cell line NUGC-3 xenografted into mice.

The composition used in the method of the present invention contains FTD and the TPI-1 in a molar ratio of 1:0.5. FTD, α,α,α-trifluorothymidine is a drug showing the growth inhibition of cancer cells through being phosphorylated by an intracellular thymidine kinase to form $F_3TMP$ which binds to a thymidine synthase to exert a DNA synthesis-inhibition. The TPI-1 is an agent preventing the inactivation of FTD due to degradation, through inhibition of the thymidine phosphorylase, a degradative enzyme for FTD.

The composition can be a composition capable of being administered orally, and a preparation containing both FTD and TPI-1, or a combination of FTD-containing and TPI-1-containing preparations. The forms of these preparations include tablets, coated tablets, pills, powders, granules, capsules, solutions, suspentions, emulsions or the like. These preparations may be formulated by any conventional formulation method generally known in the art, using a pharmaceutically acceptable carrier and the like. The preparation may be also divided conveniently for packaging so that it can be administered at a dose of 20 to 80 mg/m²/day in 2 to 4 divided portions. There is no limitation particular for the packaging method provided that it is a conventional packaging method generally known in the art; for example, tablets may be packaged in a material for moisture- and oxygen-impervious packaging.

For shaping into tablet form, the carriers may include, for example, an excipient such as lactose, sucrose, sodium chloride, glucose, urea, starch, calcium carbonate, kaolin, crystalline cellulose, or silicic acid; a binder such as water, ethanol, propanol, corn starch, simple syrup, a glucose solution, a starch solution, a gelatin solution, carboxymethylcellulose, shellac, methylcellulose, hydroxypropylcellulose, hydroxypropylmethylcellulose, potassium phosphate, or polyvinylpyrrolidone; a disintegrator such as dry starch, sodium alginate, powdered agar, powdered laminaran, sodium bicarbonate, calcium carbonate, a polyoxyethylene sorbitan fatty acid ester, sodium lauryl sulfate, monoglyceride stearate, starch, or lactose; a disintegration inhibitor such as sucrose, stearic acid, cacao butter, or hydrogenated oil; an absorption promoter such as a quaternary ammonium base, or sodium lauryl sulfate; a humectant such as glycerin or starch; an adsorbent such as starch, lactose, kaolin, bentonite, or colloidal silicic acid; and a lubricant such as purified talc, a stearate, powdered boric acid, or polyethylene glycol. In addition, the tablet may be, optionally, a tablet given a conventional coating such as a sugar-coated tablet, a gelatin-coated tablet, an enteric coated tablet, a film coated tablet, a double-coated tablet, a multiple-layer tablet, or the like.

For shaping into pill form, the carriers may include, for example, an excipient such as glucose, lactose, starch, cacao butter, hydrogenated vegetable oil, kaolin, or talc; a binder such as powdered acacia, powdered tragacanth, gelatin, or ethanol; and a disintegrator such as laminaran or agar.

The capsule is prepared by mixing the aforementioned component with various carriers as exemplified above, followed by packing the mixture in a hard gelatin capsule, a soft capsule, or the like, according to the ordinary method.

For liquid preparations for oral use, an oral solution, a syrup, an elixir, and the like may be produced according to conventional art using a flavoring agent, a buffer, a stabilizer, a smell correcting agent, or the like. The flavoring agent may be, for example, sucrose, bitter orange peel, citric acid, tartaric acid, or the like; the buffer may be, for example, sodium citrate; and the stabilizer may be, for example, tragacanth, gum arabic, gelatin, or the like.

In addition, a coloring agent, a preservative, a perfume, a seasoning, a sweetening agent, or the like, or other drugs may be optionally mixed in the above preparations, if desired.

The composition is administered at an oral dose of 20 to 80 mg/m²/day in terms of FTD in 2 to 4 divided portions. The daily dose is more preferably 25 to 75 mg/m²/day in terms of FTD, further more preferably 30 to 75 mg/m²/day, particularly 50 to 70 mg/m²/day. The dose for a patient is determined by the body surface area (BSA) calculated from the height and weight of the patient. The calculation of the body surface area is carried out using a conventional suitable method depending on the race, sex, health condition, symptom, and the like of the patient, for example, using one of the following No. 1 to No. 5, preferably No. 1 or No. 2(a) calculating formula:

1. The Mosteller formula (See N. Engl. J. Med. 1987 Oct. 22; 317 (17): 1098 (letter))

$$BSA(m^2)=([Height(cm) \times Weight(kg)]/3600)^{1/2}$$

2. The DuBois and DuBois formula (See Arch. Int. Med. 1916 17: 863-71; J. Clin. Anesth. 1992; 4 (1): 4-10)

$$BSA(m^2)=0.20247 \times Height(m)^{0.725} \times Weight(kg)^{0.425} \quad (a)$$

$$BSA(m^2)=0.007184 \times Height(cm)^{0.725} \times Weight(kg)^{0.425} \quad (b)$$

3. The Haycock formula (See The Journal of Pediatrics 1978 93: 1: 62-66)

$$BSA(m^2)=0.024265 \times Height(cm)^{0.3964} \times Weight(kg)^{0.5378}$$

4. The Gehan and George formula (See Cancer Chemother. Rep. 1970 54: 225-35)

$$BSA(m^2)=0.0235 \times Height(cm)^{0.42246} \times Weight(kg)^{0.51456}$$

5. The Boyd formula (See Minneapolis: university of Minnesota Press, 1935)

$$BSA(m^2)=0.0003207 \times Height(cm)^{0.3} \times Weight(gram)^{(0.7285-(0.0188 \times LOG(gram)))}$$

For example, when the body surface area of a cancer patient 175 cm high and 70 kg in weight is calculated by the above formula of item 1, the area is determined to be $[175 (cm) \times 70(kg)]/3600)^{1/2}=1.84$ $(m^2)$. The assumption that the dose of 60 mg/m$^2$/day is used in the patient gives 1.84× 60=111 mg, whereby the total daily dose is set to 110 mg which will be administered in 2 to 4 divided portions.

The composition of the present invention is administered in an oral dose of 20 to 80 mg/m$^2$/day in terms of FTD in 2 to 4 divided portions; however, the dose is preferably given in 2 to 3 divided portions. A dosage interval for the composition is preferably 6 hours or more.

For the method of the invention, a dosing schedule in one week can be daily administration, but, in terms of burden relief on patients, is preferably daily dosing for 5 days followed by 2 days off treatment in the week, more preferably two cycles of daily dosing for 5 days followed by 2 days off treatment in the week, and subsequent 2 weeks off treatment.

The method of the invention is intended for cancers including, but not limited to, esophageal, gastric, liver, gallbladder-bile duct, pancreatic, colorectal, head and neck, lung, breast, cervical, ovarian, bladder, prostate cancers, cancer of the testicles, soft tissue and bone sarcomas, skin cancer, malignant lymphoma, leukemia, and brain tumor, preferably malignant solid cancers such as gastric, pancreatic, breast, colorectal, head and neck, gallbladder-bile duct and lung cancers.

According to the method of the present invention, a much more favorable therapeutic effect may be obtained against cancer despite the use of the reduced dose, compared to conventional once-a-day administration. This is due to an increased amount of FTD incorporated into target site DNA resulting from administration at a daily dose in 2 to 4 divided portions. In addition, the method of the invention has facilitated the management of side effects.

EXAMPLES

Next, the present invention is described in further detail with reference to examples. However, this invention should not be construed to be limited to these examples in any manner.

Preparation Example 1

| | |
|---|---|
| FTD | 20.00 mg |
| TPI-1 | 9.42 |
| Lactose | 70.00 |
| Crystalline cellulose | 3.50 |
| Magnesium stearate | 1.00 |
| Talc | 1.00 |
| Corn starch | 3.50 |
| Hydroxypropylmethylcellulose | 25.00 |
| Per tablet | 133.42 mg |

A tablet was prepared in the preceding compounding ratio according to the ordinary method.

Preparation Example 2

| | |
|---|---|
| FTD | 15.00 mg |
| TPI-1 | 7.07 |
| Lactose | 45.00 |
| Carboxymethylcellulose | 5.00 |
| Magnesium stearate | 2.00 |
| Titanium oxide | 0.50 |
| Hydroxypropylmethylcellulose | 1.00 |
| Polyethylene glycol 4000 | 0.50 |
| per tablet | 85.07 mg |

A tablet was prepared in the preceding compounding ratio according to the ordinary method.

Preparation Example 3

| | |
|---|---|
| FTD | 30.00 mg |
| TPI-1 | 14.13 |
| Lactose | 85.00 |
| Corn starch | 100.00 |
| Hydroxypropylcellulose | 2.50 |
| Per divided dose of powders | 231.63 mg |

A granule was prepared in the preceding compounding ratio according to the ordinary method.

Preparation Example 4

| | |
|---|---|
| FTD | 10.00 mg |
| TPI-1 | 4.71 |
| Lactose | 24.00 |
| Crystalline cellulose | 12.50 |
| Magnesium stearate | 1.00 |
| Per capsule | 52.21 mg |

A capsule was prepared in the preceding compounding ratio according to the ordinary method.

Example 1

Effects of single- and divided-dosing of TAS-102 on the incorporation of FTD into DNA in mice bearing the human gastric cancer cell line NUGC-3 were studied.

Our previous data demonstrated that, when TAS-102 (the composition containing FTD and TPI in a molar ratio of 1:0.5) was orally administered to the mice at a dose of 50 mg/kg in terms of FTD, FTD levels in cancer cells could be maintained at a several-micro molar range for several hours. From this finding, we supposed that, when FTD, being divided into three times (totally, 150 mg/kg/day), would be administered at intervals of every 3 hours, tumor could contact with FTD at a several-micro molar range for 5 hours or more. Then, TAS-102 containing [$^3$H]-labeled FTD was orally administered to the cancer-bearing mice at a dose of 150 mg/kg/day in terms of FTD, and the amount of FTD incorporated into the cancer cell DNA was quantitatively determined. The results are shown in FIG. 1.

At one day after single- or divided-dosing, the amount of FTD in the DNA in the divided-dosing group was significantly increased as compared to that in the single-dosing group (p=0.002). In addition, the divided-dosing of FTD for further three consecutive days produced a significant increase in the amount of FTD in the DNA (p=0.03). These results suggested that the amount of FTD incorporated into cancer cell DNA could be enhanced by such a divided-dosing modality of TAS-102.

Example 2

Antitumor effects of single- and 3 divided-dosing of TAS-102 were studied in a cancer-bearing mouse model.

In order to confirm whether an increased incorporation of FTD into DNA as shown in FIG. 1 may lead to enhanced antitumor effects, the antitumor effects of single- and divided-dosing of TAS-102 were examined using mice xenografted with a human gastric cancer cell line (NUGC-3 or AZ-521) or a human pancreatic cancer cell line (PAN-12). The results are shown in Table 1.

When TAS-102 was administered at almost the same total dose in single- and divided-dosing (thrice a day at intervals of 3 hours) modalities, a significant antitumor effect, as compared to the control group, was observed in all the group treated with TAS-102 except for the group of mice bearing the PAN-12 cell line given TAS-102 at 150 mg/kg in a single-dosing modality. In addition, the divided-dosing of TAS-102 thrice a day at 30 mg/kg/dosing or 50 mg/kg/dosing increased the inhibition rate (IR). At the higher dosage of TAS-102 (150 mg/kg/day), the divided-dosing significantly enhanced the antitumor effect of TAS-102 against not only the cell line relatively high sensitive (AZ-521) to but also the cell line relatively low sensitive (PAN-12) to the single-dosing of TAS-102. In this respect, body weight loss used as a toxicological parameter was estimated to be −15% or less in a relative body weight loss ratio, indicating that such treatments were all tolerable.

Example 3

Therapeutic effects of TAS-102 were studied by oral administration once a day at a daily dose of 100 mg/m$^2$ in terms of FTD (trial 1) or at a daily dose of 70 mg/m$^2$ in 3 divided portions (trial 2) to cancer patients.

These trials were performed using patients with digestive cancer which is refractory to standard therapy or for which no curative therapy exists, in order to evaluate, principally, the safety of the TAS-102 administrations, representing a phase I clinical trial for determining the recommended dose (RD) at which TAS-102 can be safely administered without causing problematic side effects in phase II clinical trials carried out in each type of cancer. This phase I trial was also designed to evaluate, if possible, therapeutic effects of the administrations against tumors. For therapeutic effects against tumors, tumor-shrinking effects were determined on the basis of the comprehensive evaluation of target lesions (lesions of a measurable size, or more, depending on slice thickness) and non-target lesions (all lesions other than the target lesions), referring to the RECIST evaluation method (Journal of the National Cancer Institute, 2000, Vol 92, No. 3, 205-216). For the trial, PR (partial response) means at least a 30% decrease in the sum of the longest diameters of target lesions, maintained for a certain period of time (typically, 4 weeks) during which no progression of nontarget lesions is observed. PD (progressive disease) means at least a 20% increase in the sum of the longest diameter of target lesions, taking as reference the smallest sum longest diameter recorded since the treatment started, or unequivocal progression of existing nontarget lesions or the appearance of a new lesion(s). SD (stable disease) means neither sufficient shrinkage to qualify for PR nor sufficient increase to qualify for PD, the stopping of tumor growth, and no progression of tumor. MR (minor response) means a tumor shrinkage of less than 30%; however, it refers to a case maintaining a shrinkage near the percentage (a shrinkage of a 15% range), or temporarily showing a therapeutic response equivalent to PR.

Figure 2:
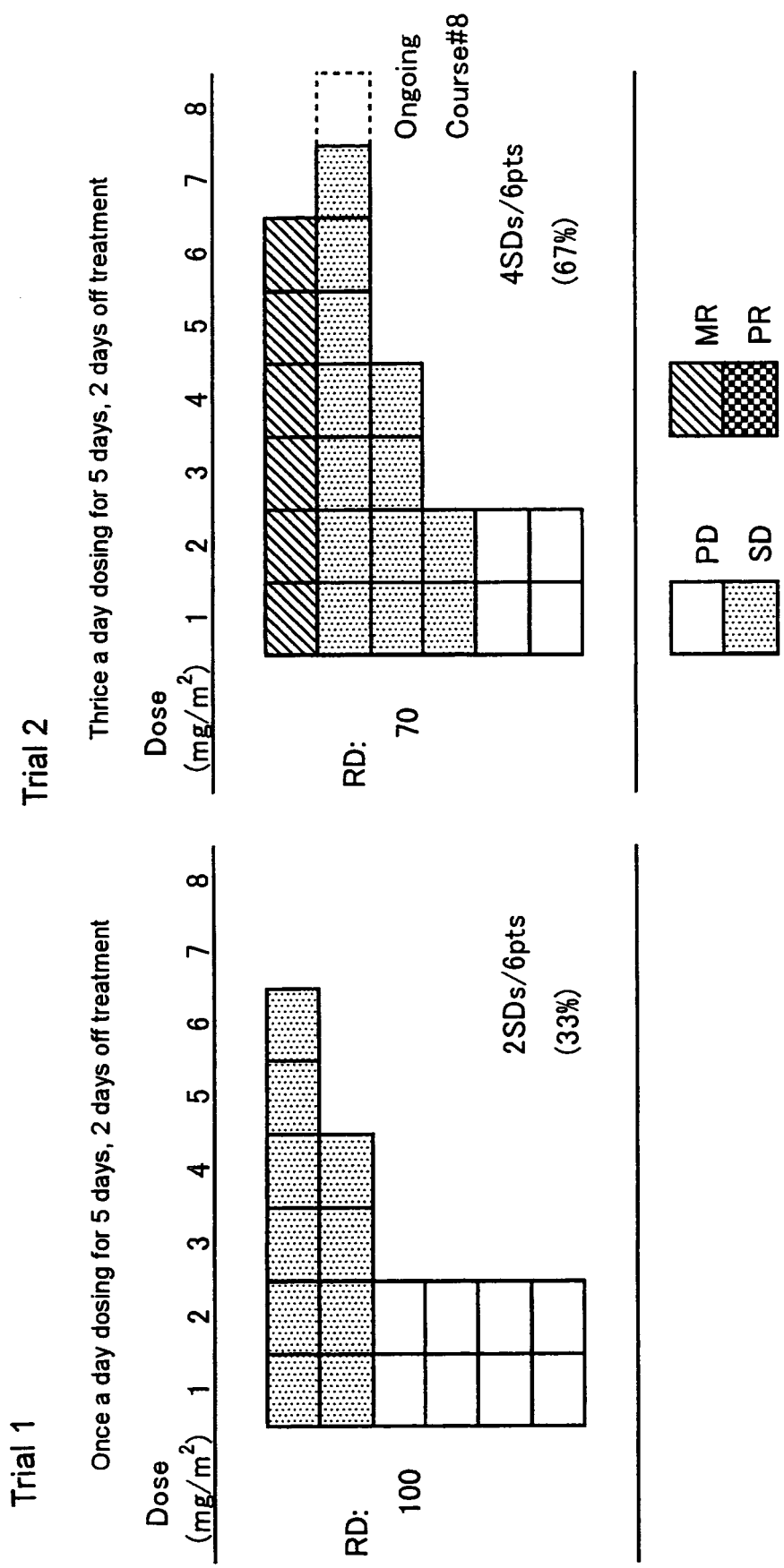

The results obtained are provided in FIG. 2. In FIG. 2, trial 1 shows the result of daily dosing of the TAS-102 preparation (tablet) at 100 mg/m$^2$ (in terms of FTD) for 5 days followed by 2 days off treatment in the week, indicating that the dosing modality was effective (stabilizing but not aggravating the tumor) in two of six cases (33%). Trial 2 shows the result of daily dosing of the preparation at 70 mg/m$^2$ (in terms of FTD) in 3 divided portions for 5 days followed by 2 days off treatment in the week, indicating that this dosing modality was effective in four of six cases (67%): the four cases reflected the stopping of tumor growth and no progression, and one of the four cases showed even tumor shrinkage. These results suggest that for TAS-102, the divided-dosing is an effective mode of administration in patients with digestive cancer which is refractory to standard therapy or for which no curative therapy exists.

Example 4

A phase I clinical trial was performed using patients with breast cancer, as described in Example 3.

Therapeutic effects of TAS-102 were studied by oral administration twice a day at 60 mg/m$^2$/day in terms of FTD (trial 3) or twice a day at 50 mg/m$^2$/day (trial 4) to patients with breast cancer, which was refractory to standard therapy or for which no curative therapy was available.

Figure 3:
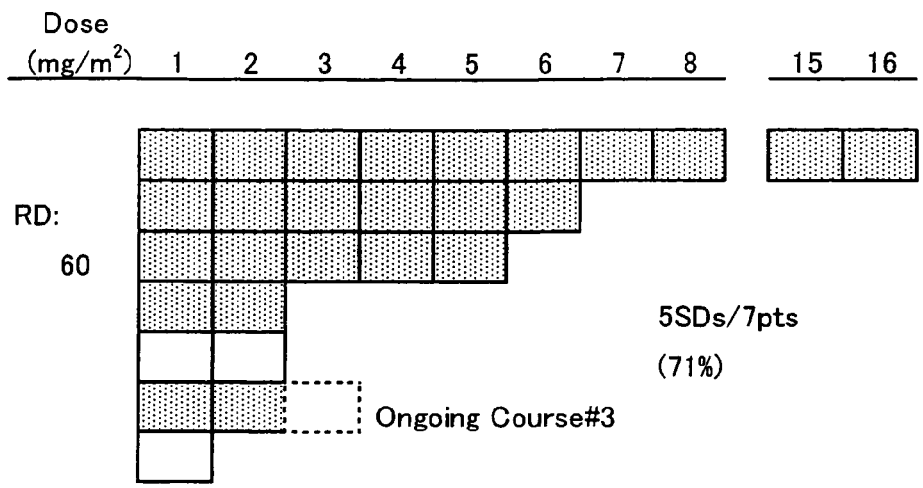
FIG. 3 is a pair of diagrams depicting a comparison of therapeutic effects on breast cancer in the case of twice-a-day oral administration between the two doses of a TAS-102 preparation containing FTD and TPI-1 (PD: progressive disease, SD: stable disease, MR: minor response, and PR: partial response). The ordinate axes represent individual patients and the horizontal axes represent the number of treatment courses. The treatment course is as described above.
Figure 3:
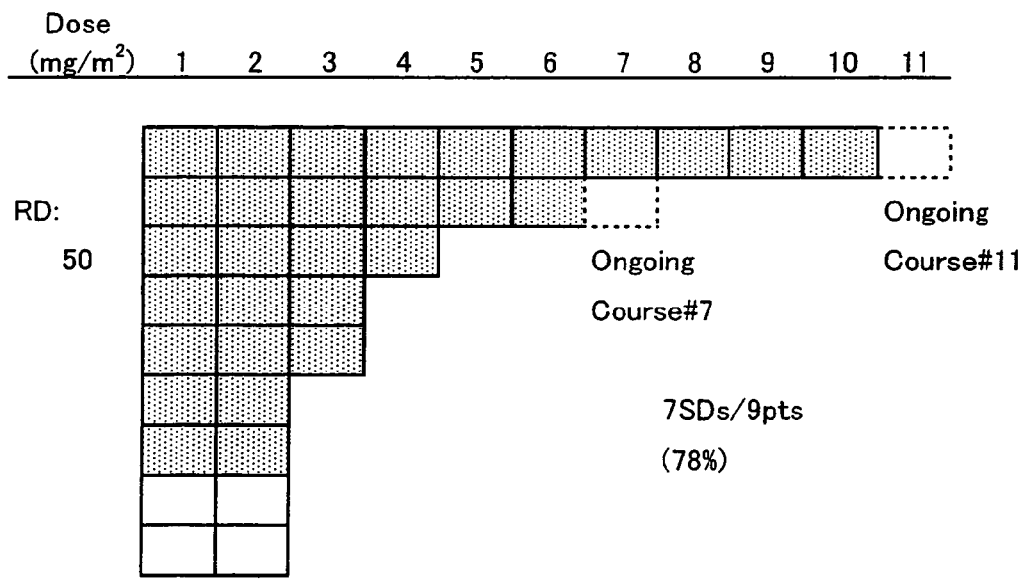
Figure 3:
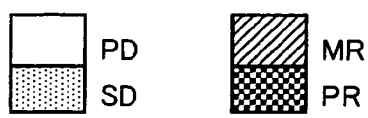

The results obtained are shown in FIG. 3. Trial 3 shows the result of daily dosing of the TAS-102 preparation (tablet) at 60 mg/m$^2$ (in terms of FTD) in 2 divided portions for 5 days followed by 2 days off treatment in the week, indicating that the dosing modality was effective in five of seven cases (71%). Trial 4 shows the result of daily dosing of the preparation at 50 mg/m$^2$ (in terms of FTD) in 2 divided portions for 5 days followed by 2 days off treatment in the week, indicating that this dosing modality was effective in seven of nine cases (78%): most cases reflected the stopping of tumor growth and no progression, and a plurality of cases had SD continued over half a year or more, including one case having SD continued over one year or more. In the case of breast cancer, it is considered that a method of treatment capable of being continued over six courses (about half a year) is excellent in clinical utility. Therefore, these results suggest that for TAS-102, the divided-dosings are effective modes of administration in patients with breast cancer which is refractory to standard therapy or for which no curative therapy exists as in the Example 1.

TABLE 1

|  | RTV[1] (mean ± SD) | | | IR[2] (%) | | | B.W.C.[3] (%) | | |
| --- | --- | --- | --- | --- | --- | --- | --- | --- | --- |
|  | AZ-521 | NUGC-3 | PAN-12 | AZ-521 | NUGC-3 | PAN-12 | AZ-521 | NUGC-3 | PAN-12 |
| SID[4], 100 | 8.57 ± 2.94 | 6.84 ± 2.38 | 8.59 ± 1.32 | 45.7 | 31.5 | 28.1 | 4.5 | 3.8 | −5.0 |
| TID[5], 30 × 3 | 6.71 ± 2.65 | 4.93 ± 1.03 | 9.33 ± 2.31 | 57.5 | 54.8 | 31.3 | −0.6 | −1.3 | −7.1 |
| SID, 150 | 5.86 ± 1.79 | 5.54 ± 1.37 | 7.34 ± 1.55 | 62.9 | 44.4 | 21.9 | 1.0 | −2.3 | −7.4 |
| TID, 50 × 3 | 2.93 ± 0.66*[6] | 4.08 ± 1.24 | 5.05 ± 1.74* | 81.4 | 62.7 | 53.0 | −4.2 | −13.8 | −14.0 |

[1] Relative tumor volume (a ratio of the estimated tumor volume on the day of response evaluation to the tumor volume on the day of animal allocation)
[2] Inhibition Rate (an inhibition rate in tumor growth)
[3] Body Weight Change (a ratio of the increased body weight to the body weight on the animal allocation day)
[4] Once-a-day dosing
[5] Thrice-a-day divided-dosing
[6] Significantly different from the SID group at a probability level of less than 0.05.

What is claimed is:

1. A method for treating at least one of a digestive cancer and a breast cancer, comprising
orally administering a composition comprising α,α,α-trifluorothymidine (FTD) and 5-chloro-6-(1-(2-iminopyrrolidinyl)methyl)uracil hydrochloride in a molar ratio of 1:0.5 at a dose of 50 to 70 mg/m$^2$/day in terms of FTD in 2 or 3 divided portions per day to a human patient in need of treatment of at least one of a digestive cancer and a breast cancer,
wherein the administration of a daily dose of said composition is in 2 or 3 portions per day for 5 days followed by 2 days off treatment in the week on a one-week dosing schedule.

2. The method according to claim 1, further comprising two cycles of administration of a daily dose of said composition in 2 or 3 portions per day for 5 days followed by 2 days off treatment in the week, and subsequent 2 weeks off treatment on a dosing schedule.

3. A method for treating at least one of a digestive cancer and a breast cancer, comprising
orally administering a composition comprising
α,α,α-trifluorothymidine (FTD) and 5-chloro-6-(1-(2-iminopyrrolidinyl)methyl)uracil hydrochloride in a molar ratio of 1:0.5 at a dose of 50 to 70 mg/m$^2$/day in terms of FTD in 2 or 3 divided portions per day to a human patient in need of treatment of at least one of a digestive cancer and a breast cancer,
wherein the α,α,α-trifluorothymidine incorporated into the target site DNA of the cancer one day after the oral administration is present in an amount that is at least a factor of 1.72 greater than the amount of α,α,α-trifluorothymidine incorporated into the target site DNA of the cancer after an equal amount of α,α,α-trifluorothymidine is orally administered in a single dose after one day.

4. A method for treating at least one of a digestive cancer and a breast cancer, comprising:
orally administering a composition comprising
α,α,α-trifluorothymidine and 5-chloro-6-(1-(2-iminopyrrolidinyl)methyl)uracil hydrochloride in a molar ratio of 1:0.5 at a dose of 50 to 70 mg/m$^2$/day in terms of α,α,α-trifluorothymidine in 2 or 3 divided portions per day to a human patient in need of treatment of at least one of a digestive cancer and a breast cancer,
wherein the α,α,α-trifluorothymidine incorporated into the target site DNA of the cancer after three days of orally administering the α,α,α-trifluorothymidine is present in an amount that is at least a factor of 1.69 greater than the amount of the α,α,α-trifluorothymidine incorporated into the target site DNA when the oral administration is carried out in a single dose for three days.

5. The method according to claim 3, wherein the composition is orally administered in 3 equally divided portions per day.

6. The method according to claim 4, wherein the composition is orally administered in 3 equally divided portions per day.

7. The method according to claim 1, wherein the cancer is breast cancer.

8. The method according to claim 3, wherein the cancer is breast cancer.

9. The method according to claim 4, wherein the cancer is breast cancer.

10. The method according to claim 1, wherein the cancer is digestive cancer.

11. The method according to claim 3, wherein the cancer is digestive cancer.

12. The method according to claim 4, wherein the cancer is digestive cancer.

* * * * *